United States Patent [19]

Shafer et al.

[11] 4,382,443

[45] May 10, 1983

[54] MATERNITY SIT-EASE PANTIES

[76] Inventors: Frances E. Shafer; Lynn O. Shafer, both of APO, New York, N.Y. 09102

[21] Appl. No.: 265,093

[22] Filed: May 19, 1981

[51] Int. Cl.³ .............................................. A61F 13/16
[52] U.S. Cl. .................................. 604/396; 604/398; 604/373
[58] Field of Search .................................... 128/98–99, 128/106, 159, 160, 168, 288, 286, 289, 290 H

[56] References Cited

U.S. PATENT DOCUMENTS

| | | | |
|---|---|---|---|
| 2,333,839 | 11/1943 | Blackburn et al. | 128/98 |
| 2,494,292 | 1/1950 | Frazer | 128/288 |
| 3,116,736 | 1/1964 | Alberts | 128/98 |
| 3,312,981 | 4/1967 | McGuire et al. | 128/288 |

*Primary Examiner*—C. Fred Rosenbaum
*Attorney, Agent, or Firm*—Kemon & Estabrook

[57] ABSTRACT

A nether garment of the bifurcated underwear type having mounted on the crotch segment rearwardly of the central portion thereon a pair of spaced parallel pockets. The pockets are configured to receive pads or blocks of suitable cushiony material capable of supporting the garment wearer's body in certain desired areas. The pocketed pads or blocks tend to relieve or restrict pressure that would normally be applied to the areas of the wearer's body located between said pads or blocks.

9 Claims, 5 Drawing Figures

U.S. Patent  May 10, 1983  4,382,443
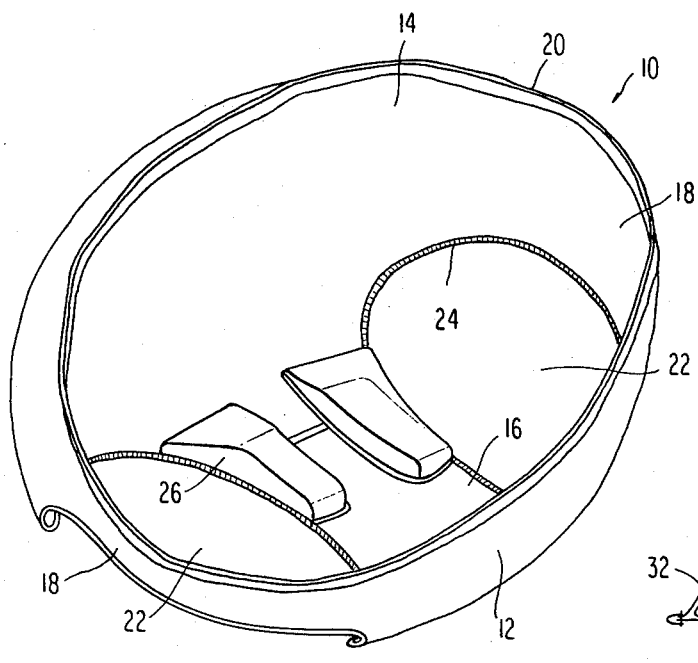
FIG. 1
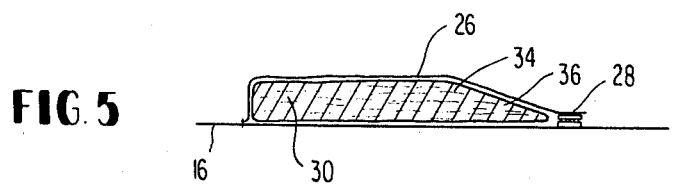
FIG. 4
FIG. 5
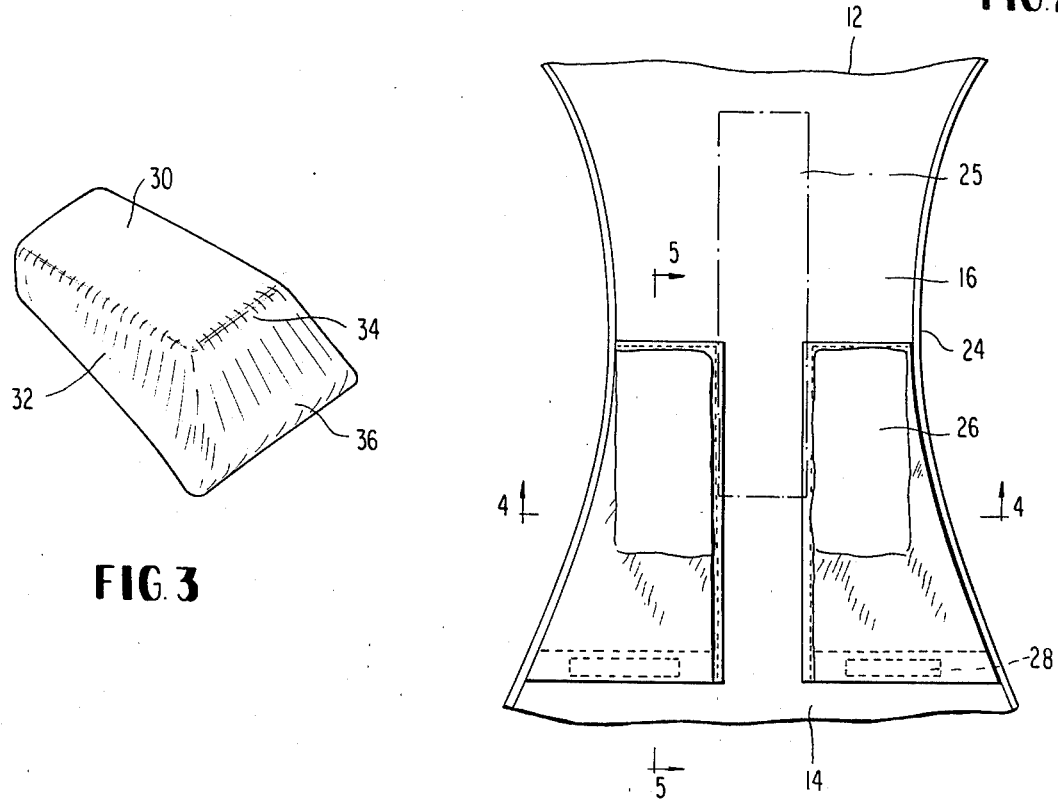
FIG. 3
FIG. 2

MATERNITY SIT-EASE PANTIES

BACKGROUND OF THE INVENTION

The present invention applies to underwear of the type commonly referred to as panties or shorts which have supporting pads or blocks positioned therein to receive and support the weight of the wearer in certain areas.

In the past when a person has been recuperating from childbirth or hemorrhoidectomy or some similar type of operation the customary procedure has been to utilize an inflated rubber ring or tube. The ring engaged the wearer's body so as to provide sufficient support therefor while at the same time maintaining the affected area in spaced relation from a supporting surface such as a chair or bench. While the ring accomplished its objectives it definitely limited or restricted a person's activities and movements to a very large degree.

SUMMARY OF THE INVENTION

The present invention is directed to a bifurcated undergarment of the panty type having a crotch area of a size to hold a catamenial receiver as well as a pair of spaced pockets having pads or blocks positioned therein. The pads or blocks are configured to conform to the contour of the wearer's body so as to support the weight of the body in a sitting position. This arrangement enables the wearer to sit comfortably while the affected area is healing yet does no restrict the mobility of the wearer or require the use of any special configured external supporting members.

BRIEF DESCRIPTION OF THE DRAWINGS

FIG. 1 is a perspective view of a bifurcated undergarment embodying the present invention;

FIG. 2 is a plan view of the crotch portion of the garment of FIG. 1 showing the pockets for the pads or blocks;

FIG. 3 is a perspective view of a pad or block for one of the pockets shown in FIG. 2;

FIG. 4 is a vertical sectional view of the pockets with pads or blocks therein, the view being taken on line 4—4 of FIG. 2; and FIG. 5 is a vertical sectional view of one of the pockets with a pad or block therein, the view being taken on line 5—5 of FIG. 2.

DESCRIPTION OF THE PREFERRED EMBODIMENT

There is shown in FIG. 1 a bifurcated nether garment 10, of the panty type, having a front panel portion 12 and a rear panel portion 14 joined to one another by a crotch segment 16 to form a unitary structure. The upper portion of the front panel 12 is joined to the upper portion of the rear panel 14 by side segments 18 and a suitable elastic waistband 20 is secured to the upper edge of said panels. The front, side and rear panels are all configured to define suitable leg openings 22 which are provided with elastic leg bands 24. The various panels constituting the panty garment of the present invention are preferrable formed from a suitable stretchable type of material, such as nylon spandex, so as to assume a snug fit while at the same time remaining in proper position on the wearer's body.

The crotch segment 16 is defined by accurate segments of the leg openings 22, as illustrated in FIGS. 1 and 2, with the portion of the crotch segment where it merges with the back panel portion 14 being of a slightly wider width than the corresponding area that merges into the front panel 12. The crotch segment 16 has positioned thereon, in approximately the central portion thereof, a catamenial/lochia receiver 25 with suitable convential fastening means, not shown, being provided to secure and maintain the catamenial/lochia receiver on the crotch segment. The crotch segment 16 is provided with a pair of pockets 26 which are positioned adjacent to and on opposite sides of the catamenial receiver with the front or smaller ends of the pockets terminating in the vicinity of the middle of the crotch segment. The rear or larger ends of the pockets 26 extend beyond the rear end of the catamenial receiver and into the area where the crotch segment 16 merges into the back panel 14. The rearmost end portion of the pockets 26 are provided with suitable fastening means 28 which could take the form of the well known "VELCRO" fasteners. The pockets 26 are adapted to receive suitable pads 30.

The pads 30 are tapered from front to rear with the narrow end being positioned in the front end of the pocket 26 and the wide end merging into the back panel 14 at its junction with the crotch segment 16 yet still retained within the pockets 26. The pads 30 are of uniform thickness throughout the major portion of their area with the area adjacent the catamenial receiver being an area of uniform thickness with a slight taper being provided along the outer edge 32, FIG. 4, adjacent the leg bands 24. The rear end portion 34 of each pad 30 is tapered at 36, FIG. 5, so as to preclude any bunching of the pad when the wearer is in a sitting position. The pads 30 may be formed from a synthetic rubber material or of the material commonly employed in sanitary napkins or even a disposable pad formed from paper or cottom.

The pads 30 may be formed from any suitable material that is soft enough for sitting comfort yet provides sufficient rigidity to wherein the wearer of the panty garment will sit above the catamenial receiver so that the wearer's body weight will not rest on the episiotomy or other tender area. The pad 30, depending upon the type of material from which they are formed may have their upper surfaces slightly concaved so as to tend to fit the natural curve of the human body particularly when the wearer is in a sitting position.

In the use or wearing of the garment embodying the present invention the pads 30 are inserted into the pockets 26 and the fasteners 28 are then secured in the normal manner. The wearer then positions the garment upon the body where same will be retained in proper position with a snug fit in view of the material from which the garment is made. The configuration of the pads 30, and, there positioning on opposite sides of the catamenial receiver from approximately the medium portion thereof and extending beyond its rear most end portion to approximately the area of mergence of the crotch segment with the back panel, will enable the wearer to sit upon the pads with the wearer's body being supported above the catamenial receiver in comfort without applying pressure to the eposiotomy or other tender area.

Although the foregoing description is necessarily of a detailed character in order that the invention maybe completely set forth, it is to be understood that the specific terminology is not intended to be restrictive or confining, and that various rearrangements of parts and modifications of detail may be resorted to without departing from the scope or spirit of the invention as herein claimed.

I claim:

1. In a bifurcated nether garment having a front panel joined to a rear panel by side segments and a crotch segment with elastic bands encompassing the waist and leg openings, a catamenial receiver secured to said crotch segment in the central portion thereof with the longitudinal axis of said catamenial receiver coinciding with the longitudinal axis of said crotch segment, a pair of pockets secured to said crotch segment on opposite sides of said catamenial receiver with the longitudinal axis of said pockets being parallel to the longitudinal axis of said crotch segment, said pockets projecting towards said rear panel and pad members positioned in said pockets for supporting the body weight of a wearer of said garment in a sitting position to maintain the body of said wearer spaced from said catamenial receiver.

2. A garment as set forth in claim 1 wherein the width of the forward end of said pockets is less than the width of the rear end of said pockets.

3. A garment as set forth in claim 1 wherein the rear end of said pockets merge into said rear panel and the front end of said pockets are positioned in the center portion of said crotch segment.

4. A garment as set forth in claim 3 wherein the rear portion of said pockets are provided with fastening means.

5. A garment as set forth in claim 2 wherein said pads are of a size commensurate with the size of said pockets.

6. A garment as set forth in claim 1 wherein said pads are formed of a resilient material that is sufficiently rigid enough to support the body weight of the wearer to maintain the eposiotomy of said wearer spaced from said catamenial receiver.

7. A garment as set forth in claim 1 wherein said pads terminate in a tapered out edge portion that terminates at the outer edge of the crotch segment.

8. A garment as set forth in claim 1 wherein said pads are of uniform thickness in the forward portion adjacent the catamenial receiver and then gradually taper towards the rear end portion.

9. A garment as set forth in claim 2 wherein the forward end of said pads are positioned rearwardly of the median axis of said catamenial receiver and extended beyond the rear end of said catamenial receiver onto the crotch segment and said rear panel.

* * * * *